United States Patent [19]
Silverstein et al.

[11] Patent Number: 5,725,499
[45] Date of Patent: Mar. 10, 1998

[54] DUAL BARRELED SYRINGE AND METHODS OF ASSEMBLY AND USE

[75] Inventors: Jerome Silverstein, North Franklin; Charles Frey, Bozrah, both of Conn.

[73] Assignee: Plas-Pak Industries, Inc., Norwich, Conn.

[21] Appl. No.: 241,294

[22] Filed: May 11, 1994

[51] Int. Cl.$^6$ ............................................. A61M 37/00
[52] U.S. Cl. ............................ 604/82; 604/87; 604/218; 222/145.1
[58] Field of Search ................... 604/82, 87, 191, 604/218, 220, 226, 228, 244, 111, 200; 222/135, 137, 145

[56] References Cited

U.S. PATENT DOCUMENTS

| | | | |
|---|---|---|---|
| 758,949 | 5/1904 | Apple et al. | 604/200 |
| 3,828,775 | 8/1974 | Armel | 604/200 |
| 3,908,654 | 9/1975 | Lhoest et al. | 604/200 |
| 3,952,920 | 4/1976 | Bergman | 222/137 |
| 4,040,420 | 8/1977 | Speer | 604/191 |
| 4,631,055 | 12/1986 | Redl et al. | 604/191 |
| 4,978,336 | 12/1990 | Capozzi et al. | 604/191 |
| 5,290,259 | 3/1994 | Fischer | 604/218 |
| 5,328,462 | 7/1994 | Fischer | 604/191 |
| 5,368,563 | 11/1994 | Lonneman et al. | 604/82 |

*Primary Examiner*—Corrine M. McDermott
*Assistant Examiner*—Cris L. Rodriguez
*Attorney, Agent, or Firm*—John H. Crozier

[57] ABSTRACT

In one preferred embodiment, a body for a dual barreled syringe, said body including: two, parallel, cylindrical, hollow, cojoined, barrels having, respectively, open filling ends and closed discharge ends from which discharge ends axially extend discharge nozzles; and sealing apparatus, closing the discharge ends, formed monolithically with and sealing distal ends of the discharge nozzles, the sealing apparatus being manually severable from the distal ends of the discharge nozzles so as to open the discharge nozzles to permit the discharge therefrom of material held within the barrels, without the sealing apparatus being mechanically cut from the discharge nozzles. In another preferred embodiment, there is provided a plunger assembly for a dual barreled syringe, the plunger assembly including: two parallel plungers cojoined at first ends thereof against which manual pressure may be applied to force sealing members disposed at a second end thereof through barrels of a body of the dual barreled syringe to discharge materials from the barrels; and joining apparatus, spaced from the flange, attached to, extending between, and joining the plungers to maintain the plungers in relatively rigid, parallel alignment.

5 Claims, 2 Drawing Sheets

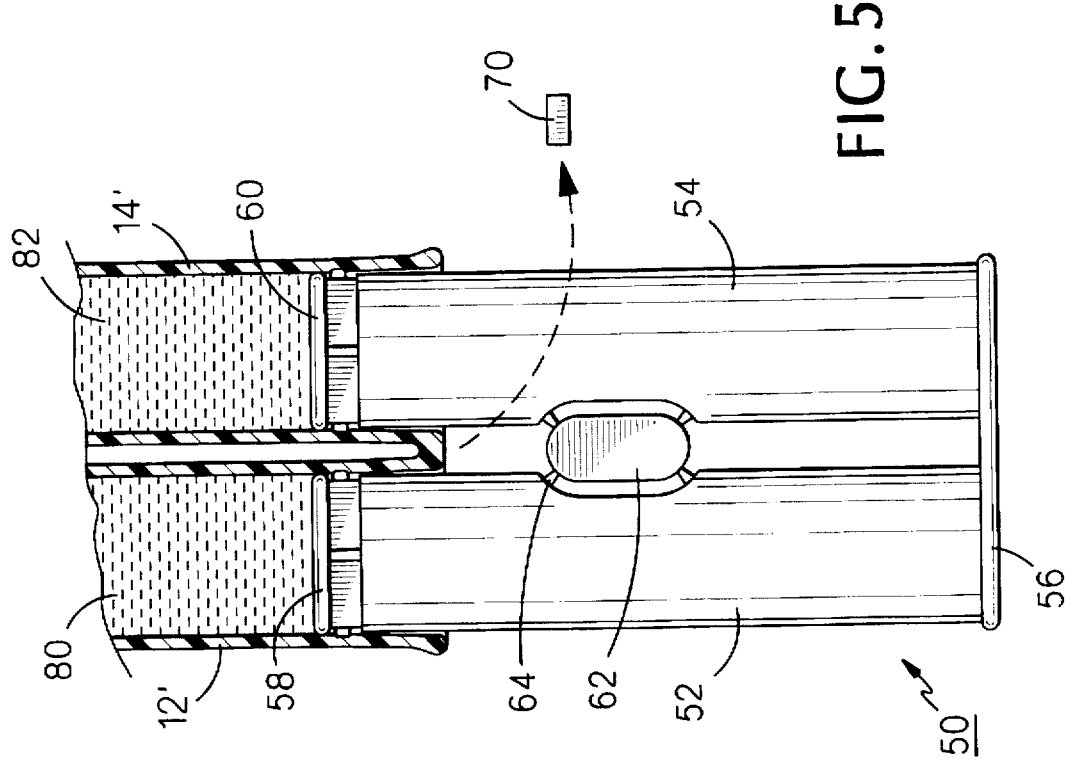
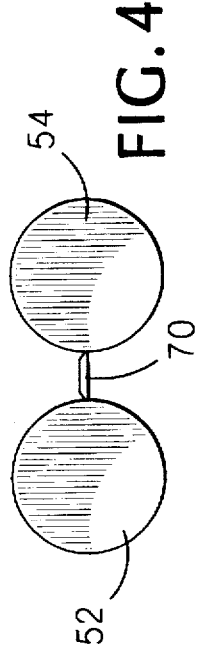
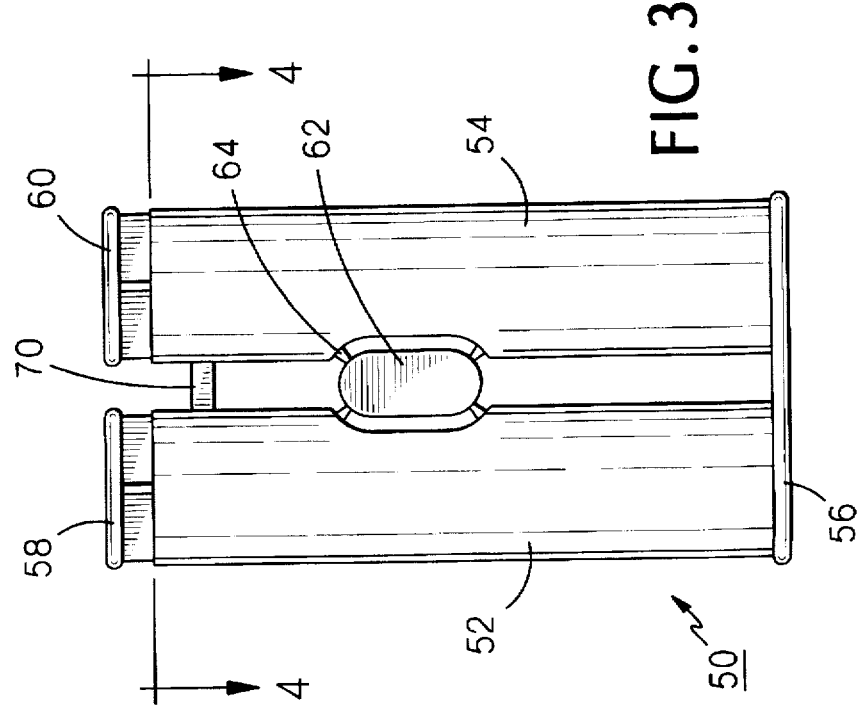

DUAL BARRELED SYRINGE AND METHODS OF ASSEMBLY AND USE

BACKGROUND OF THE INVENTION

1. Field of the Invention

The present invention relates to liquid dispensing syringes generally and, more particularly, but not by way of limitation, to a novel dual barreled syringe that is simple to assemble and use.

2. Background Art

There are circumstances in which it is desirable to dispense liquid or semi-liquid materials in a predetermined ratio. The materials may include reactive, two component adhesives, sealants, coating, or potting compounds, in which one material may comprise a resin compound and the other material a catalyst. The chemical families of such materials include epoxies, acrylics, silicones, polyesters, urethanes, polyurethane foams, and hybrid and reactive elastomers and adhesives.

In some cases, particularly in the past, it was necessary to separately dispense one of two materials and then the other of the materials, following which they were mixed. Various devices have been developed to simultaneously dispense the materials. Such a device, particularly for smaller quantities of materials, typically comprise a syringe having two, parallel, cylindrical bores, or barrels, with two joined plungers insertable in one end of the barrels and axially moveable therewithin, which plungers are manually forced against the materials in the bores to dispense the materials from nozzles formed at the other end of the bores.

These devices are sold with the plungers partially inserted in the bores, thus sealing the bores at one end, and the nozzles are sealed with individual caps molded over the distal ends of the nozzles. In order to initially dispense materials from the devices, the user must first sever the caps from the nozzles with a knife, razor blade, or similar sharp tool. Since the material is usually rather hard, this can be a hazardous operation. Also, this is often a messy operation, since material is prone to leak from the first nozzle which has been opened while the second nozzle is being opened. This is aggravated by manual pressure which may be applied to the barrels while severing the second cap.

A further problem with such conventional dual barrel syringes occurs in the assembly thereof. In use, the two plungers must necessarily have no common attachment means, except at the distal ends thereof where pressure is applied to dispense materials from the nozzles of the barrels. This arrangement somewhat complicates assembly of the plungers in the barrels, since the free ends of the plungers which must be inserted in the bores of the cartridge, are free to move with respect to each other.

Accordingly, it is a principal object of the present invention to provide a dual barrel syringe and method of use which eliminates the problems inherent in having nozzle sealing caps which must be cut from the ends of the nozzles.

It is a further object of the invention to provide a dual barrel syringe and method of assembly which eliminates assembly problems inherent in conventional dual barrel syringes.

It is an additional object of the invention to provide such dual barrel syringes which are economically and easily manufactured.

Other objects of the present invention, as well as particular features, elements, and advantages thereof, will be elucidated in, or be apparent from, the following description and the accompanying drawing figures.

BRIEF DESCRIPTION OF THE DRAWING

Understanding of the present invention and the various aspects thereof will be facilitated by reference to the accompanying drawing figures, submitted for purposes of illustration only and not intended to define the scope of the invention, on which:

FIG. 3 is a side elevational view of a plunger assembly for use in a dual barrel syringe.

FIG. 4 is a top plan view taken along line "4—4" of FIG. 3.

FIG. 5 is a side elevational view of the plunger of FIG. 3 being inserted in the body of a dual barrel syringe.

DETAILED DESCRIPTION OF THE PREFERRED EMBODIMENTS

Figure 1:
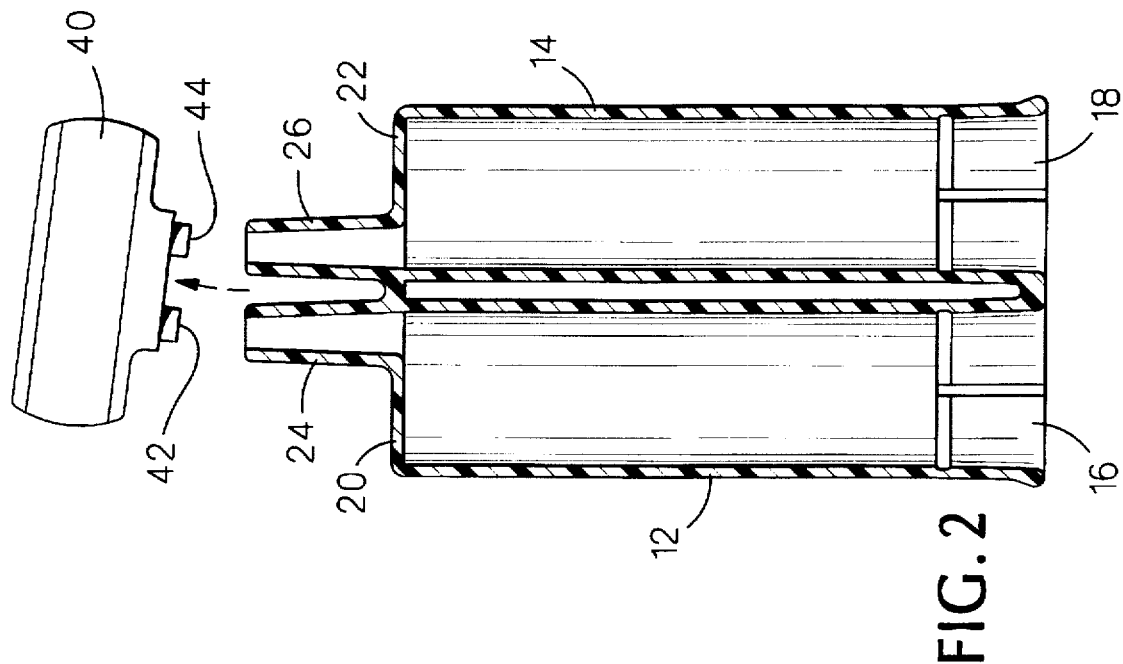
FIG. 1 is side elevational view, in cross-section, of the body of a dual barrel syringe constructed according to the present invention, with the nozzles thereof sealed.

Reference should now be made to the drawing figures, on which similar or identical elements are given consistent identifying numerals throughout the various figures thereof, and on which parenthetical references to figure numbers direct the reader to the view(s) on which the element(s) being described is (are) best seen, although the element(s) may be seen also on other views.

FIG. 1 illustrates a dual barrel syringe body, generally indicated by the reference numeral 10, constructed according to the present invention. Body 10 includes two, parallel, cylindrical, hollow barrels 12 and 14 having, respectively, open filling ends 16 and 18 and closed discharge ends 20 and 22 from which axially extend discharge nozzles 24 and 26. Barrels 12 and 14 are cojoined at filling ends 16 and 18 and at closed discharge ends 20 and 22. As so far described, body 10 is typical of conventional dual barreled syringes.

The present invention provides, for sealing the distal ends of discharge nozzles 24 and 26, an elongate tab 40 from which depend cylindrical sealing hubs 42 and 44 which are monolithic with, respectively, the upper inner peripheral edges of discharge nozzles 24 and 26.

All of the foregoing components of dual barreled syringe body 10 are molded together in a single conventional injection molding process from a suitable polymeric material, such as clear polypropylene, for example.

Figure 2:
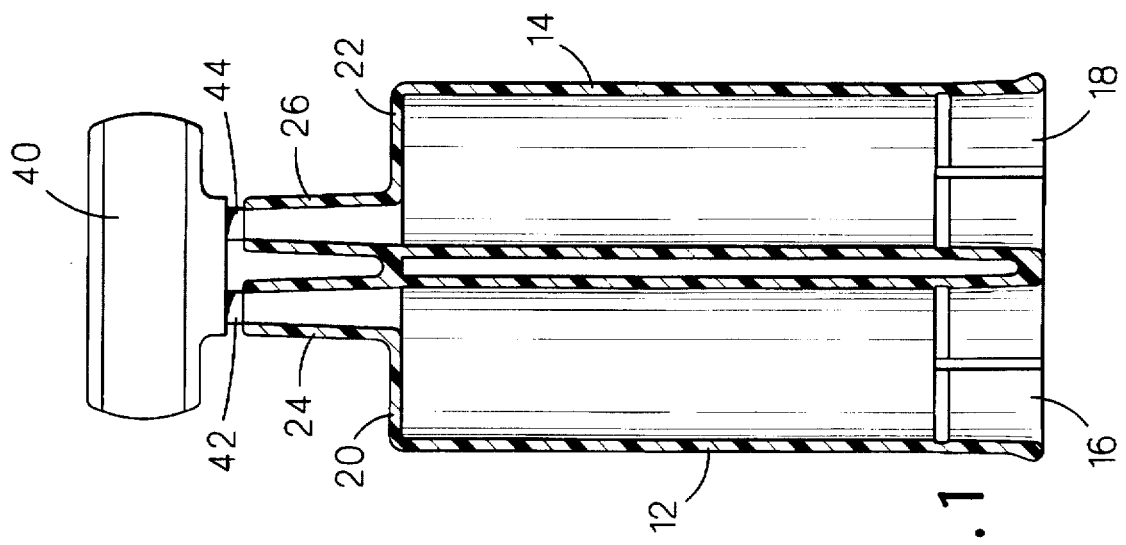
FIG. 2 is a side elevational view, in cross-section, of the syringe of FIG. 1 with the nozzles thereof opened.

Referring now to FIG. 2, sealing hubs 42 and 44 are severable from the distal ends of discharge nozzles 24 and 26 by manually bending tab 40 away from the major axes of barrels 12 and 14 to simultaneously sever the nubs and open the discharge nozzles. Tab 40 is then discarded. Materials (not shown) are then dispensed from body 10 and discharge nozzles 24 and 26 are then closed with a sealing cover (not shown), as with conventionally constructed dual barreled syringes. The operation is performed quickly, without the use of any tool, and with little opportunity for leakage of contents of body 10.

FIG. 3 illustrates a plunger assembly, generally indicated by the reference numeral 50, and constructed according to the present invention. Plunger assembly 50 includes two, parallel plungers 52 and 54 cojoined by a flange 56 against which manual pressure may be applied to force sealing members 58 and 60 through, respectively, barrels 12 and 14 (FIG. 1) to discharge materials (not shown) from the barrels. A sealing cap 62 is removably held between plungers 52 and 54 by means of thin, narrow legs, as at 64, which may be manually severed easily to permit the sealing cap to be removed and placed on the open distal ends of discharge nozzles 24 and 26 (FIG. 2), in the manner of conventionally constructed dual barreled syringes. As so far described, plunger assembly is conventional.

The present invention maintains plungers 52 and 54 in relatively rigid, parallel alignment by providing a bridge 70, extending between and joining barrels 52 and 54 near the end of the plungers bearing sealing members 58 and 60. As seen on FIG. 4, the ends of bridge 70 are thinned where they are attached to barrels 52 and 54.

All of the foregoing components of plunger assembly 50 are molded together in a single conventional injection molding process from a suitable polymeric material, such as medium density polyethylene, for example.

Reference should now be made to FIG. 5 which illustrates plunger assembly 50 with plungers 52 and 54 partially inserted in barrels 12' and 14' of a dual barreled syringe body 10', the barrels having been filled with liquid materials 80 and 82. The configuration shown is that in which the assembly normally would be sold. Dual barreled syringe body 10' may or may not be of the construction of dual barreled syringe body 10 (FIG. 1). Conventional automatic machinery is employed to insert plunger assembly 50 into body 10'. In the present invention, the presence of bridge 70 facilitates this insertion step by keeping barrels 52 and 54 parallely aligned. When the degree of insertion is such that bridge 70 reaches the lower edge of cojoined barrels 12' and 14', further insertion causes the thin ends of the bridge (FIG. 4) to be severed from plungers 52 and 54, as shown on FIG. 5, so that further insertion is not prevented by the bridge.

It will thus be seen that the objects set forth above, among those elucidated in, or made apparent from, the preceding description, are efficiently attained and, since certain changes may be made in the above construction without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

We claim:

1. A plunger assembly for a dual barreled syringe, said plunger assembly comprising:
   (a) two parallel plungers cojoined by a flange at first ends thereof against which manual pressure may be applied to force sealing members disposed at a second end thereof through barrels of a body of said dual barreled syringe to discharge materials from said barrels; and
   (b) joining means, spaced from said flange, attached to, extending between, and joining said plungers to maintain said plungers in relatively rigid, parallel alignment.

2. A plunger assembly, as defined in claim 1, wherein: said joining means comprises a bridge disposed near said second end of said plungers and extending therebetween.

3. A plunger assembly, as defined in claim 1, wherein: said bridge is severable from said barrels by the action of inserting said first and second plungers into said first and second barrels.

4. A method of assembling a dual barreled syringe, said method comprising:
   (a) providing parallel plungers cojoined at first ends thereof and having sealing means at second ends thereof;
   (b) providing a syringe body having therein two parallel barrels;
   (c) providing joining means, spaced from said first ends, attached to, extending between, and joining said plungers to maintain said plungers in relatively rigid, parallel alignment; and
   (d) severing said joining means from said plungers by the action of inserting said plungers into said barrels.

5. A method, as defined in claim 4, further comprising: providing said bridge disposed near said second ends of said plungers.

* * * * *